US012702952B2

(12) United States Patent
Shmidt et al.

(10) Patent No.: US 12,702,952 B2
(45) Date of Patent: Aug. 11, 2026

(54) METHOD FOR PURIFYING LIQUID AND SYSTEM FOR THE IMPLEMENTATION THEREOF

(71) Applicant: Electrophor Inc., Woodmere, NY (US)

(72) Inventors: Joseph Lvovich Shmidt, New York, NY (US); Yurij Vladimirovich Tatuev, St. Petersburg (RU); Evgenij Anatoljevich Zotkin, St. Petersburg (RU); Mikhail Grigorjevich Vinogradov, St. Petersburg (RU)

(73) Assignee: ELECTROPHOR INC., Woodmere, NY (US)

( * ) Notice: Subject to any disclaimer, the term of this patent is extended or adjusted under 35 U.S.C. 154(b) by 215 days.

(21) Appl. No.: 15/317,484

(22) PCT Filed: Apr. 6, 2015

(86) PCT No.: PCT/RU2015/000216
§ 371 (c)(1),
(2) Date: Dec. 9, 2016

(87) PCT Pub. No.: WO2015/190948
PCT Pub. Date: Dec. 17, 2015

(65) Prior Publication Data

US 2017/0136411 A1 May 18, 2017

(30) Foreign Application Priority Data

Jun. 10, 2014 (RU) ......................... RU20140123820

(51) Int. Cl.
*B01D 61/02* (2006.01)
*A23L 2/08* (2006.01)
(Continued)

(52) U.S. Cl.
CPC ............ *B01D 61/026* (2022.08); *A61L 2/022* (2013.01); *B01D 37/00* (2013.01); *B01D 61/025* (2013.01);
(Continued)

(58) Field of Classification Search
CPC ...... B01D 61/022; B01D 61/10; B01D 61/08; B01D 61/025; B01D 61/06; B01D 65/02;
(Continued)

(56) References Cited

U.S. PATENT DOCUMENTS

| | | |
|---|---|---|
| 2,910,836 A | 11/1959 | Karrer |
| 3,493,496 A | 2/1970 | Bray |

(Continued)

FOREIGN PATENT DOCUMENTS

| | | |
|---|---|---|
| CN | 101732901 | 6/2010 |
| CN | 107108267 | 8/2017 |

(Continued)

OTHER PUBLICATIONS

International Search Report for PCT/RU2016/000466 mailed Jan. 12, 2017; 1 page.

(Continued)

*Primary Examiner* — Benjamin L Lebron
*Assistant Examiner* — Bernadette Karen Mcgann
(74) *Attorney, Agent, or Firm* — Fitch, Even, Tabin & Flanner LLP

(57) ABSTRACT

The present liquid purification method, carried out with the aid of a liquid purification system, includes a three-stage liquid filtration cycle, during which all of the drain liquid can be continuously fed back into the purification system until the liquid filtration cycle is complete. During this continuous recycling, a high liquid flow rate is maintained, and the feed rate of the liquid can be controlled during the continuous mixing of initial liquid and drain liquid. The
(Continued)

common aim of this subject matter and the technical result achieved in the use of same is the development of a novel energy-efficient method and system for purifying liquids which makes it possible to improve the energy-efficiency of liquid purification while simultaneously increasing the degree of purification and the extent to which the initial liquid is used.

18 Claims, 2 Drawing Sheets

(51) Int. Cl.

| | |
|---|---|
| ***A61L 2/022*** | (2026.01) |
| ***B01D 37/00*** | (2006.01) |
| ***B01D 61/06*** | (2006.01) |
| ***B01D 61/08*** | (2006.01) |
| ***B01D 61/10*** | (2006.01) |
| ***B01D 65/02*** | (2006.01) |
| ***C02F 1/44*** | (2023.01) |
| ***C02F 9/00*** | (2023.01) |
| ***C13B 20/16*** | (2011.01) |

(52) U.S. Cl.
CPC ............. *B01D 61/06* (2013.01); *B01D 61/08* (2013.01); *B01D 61/10* (2013.01); *B01D 65/02* (2013.01); *C02F 1/44* (2013.01); *C02F 9/00* (2013.01); *C13B 20/165* (2013.01); *A23L 2/082* (2013.01); *B01D 2201/202* (2013.01); *B01D 2311/12* (2013.01); *B01D 2311/14* (2013.01); *B01D 2311/20* (2013.01); *B01D 2311/2523* (2022.08); *B01D 2311/2626* (2013.01); *B01D 2313/24* (2013.01); *B01D 2313/246* (2013.01); *B01D 2315/10* (2013.01); *B01D 2315/12* (2013.01); *B01D 2321/04* (2013.01); *C02F 1/441* (2013.01); *C02F 1/442* (2013.01); *C02F 2301/046* (2013.01); *Y02A 20/131* (2018.01)

(58) Field of Classification Search
CPC ............ B01D 37/00; B01D 2311/2626; B01D 2311/25; B01D 2315/10; B01D 2313/246; B01D 2321/04; B01D 2311/20; B01D 2313/24; B01D 2311/12; B01D 2315/12; B01D 2201/202; B01D 2311/14; B01D 2313/26; B01D 61/026; C02F 9/00; C02F 1/44; C02F 2301/046; C02F 1/441; C02F 1/442; Y02A 20/131; A61L 2/022; C13B 20/165; A23L 2/082
See application file for complete search history.

(56) References Cited

U.S. PATENT DOCUMENTS 3,794,172 A 2/1974 Bray
4,086,166 A 4/1978 Martin
4,176,063 A 11/1979 Tyler
4,243,523 A 1/1981 Pelmulder
4,414,113 A 11/1983 Laterra
4,626,346 A 12/1986 Hall
4,704,210 A 11/1987 Boze
4,833,888 A 5/1989 Kerner
4,891,594 A 1/1990 Wilfley
4,921,610 A 5/1990 Ford
4,931,186 A 6/1990 Ford
4,935,143 A 6/1990 Kopp
4,973,404 A 11/1990 Weber
4,981,594 A 1/1991 Jones
4,983,301 A 1/1991 Szuecz
4,997,553 A 3/1991 Clack
5,024,762 A 6/1991 Ford
5,049,272 A 9/1991 Nieweg
5,266,203 A * 11/1993 Mukhopadhyay ... B01D 61/022 210/638
5,503,735 A 4/1996 Vinas
6,068,764 A 5/2000 Chau
6,093,312 A 7/2000 Boulter
6,103,125 A 8/2000 Kuepper
6,120,688 A 9/2000 Daly
6,162,361 A * 12/2000 Adiga ................. B01D 61/142 204/450
6,190,558 B1 2/2001 Robbins
6,290,856 B1 9/2001 Beall
6,331,253 B1 * 12/2001 Schrive ................. C10G 31/09 210/652
6,355,173 B1 3/2002 Den Bieman
7,285,210 B2 10/2007 Schmitt
7,338,595 B2 3/2008 Vannewenhizen et al.
7,601,256 B2 10/2009 Beall
7,628,921 B2 12/2009 Efraty
8,147,700 B2 4/2012 Elektorowicz
8,652,331 B2 2/2014 Zha
9,550,150 B2 1/2017 Smirnov
10,399,870 B2 9/2019 Clark
10,562,787 B2 2/2020 Hoek
10,954,141 B2 3/2021 Wilson
11,439,955 B2 9/2022 Shmidt
2002/0011443 A1 1/2002 Komatsu
2002/0100716 A1 8/2002 Bosko
2005/0023198 A1 2/2005 Halemba
2005/0109703 A1 * 5/2005 Newenhizen .......... B01D 61/08 210/739
2007/0062870 A1 3/2007 Chen
2007/0151925 A1 * 7/2007 de los Reyes ......... B01D 61/14 210/641
2009/0113898 A1 5/2009 Kirol
2009/0152197 A1 6/2009 Lilas
2010/0018220 A1 1/2010 Modad
2011/0180465 A1 7/2011 Richetti
2011/0198275 A1 * 8/2011 Hayes ..................... C02F 1/441 210/257.2
2011/0303660 A1 * 12/2011 Yang ..................... B01D 61/10 220/23.83
2012/0048790 A1 3/2012 Voelker
2012/0055858 A1 3/2012 Collins
2012/0168368 A1 7/2012 De Los Reyes
2012/0234739 A1 9/2012 Smirnov
2013/0126430 A1 * 5/2013 Kenley ................. B01D 61/00 210/638
2013/0334115 A1 12/2013 Voelker
2014/0061129 A1 3/2014 Hoz
2014/0110337 A1 4/2014 Hoz
2016/0046503 A1 2/2016 Hoek
2017/0209834 A1 7/2017 Cohen
2018/0251385 A1 9/2018 Clark
2020/0140286 A1 5/2020 Hoek
2020/0283309 A1 9/2020 Reid
2022/0032218 A1 2/2022 Shmidt
2022/0220007 A1 7/2022 Reid

FOREIGN PATENT DOCUMENTS

CN 107250063 10/2017
CN 108473341 8/2018
CN 108473342 8/2018
DE 102006015675 A1 10/2007
DE 202011000680 9/2011
DE 16842406 11/2018
DE 16842407 11/2018
EP 0479492 4/1992
EP 1183212 3/2002
EP 3241807 11/2017
EP 3345871 7/2018
EP 3345872 7/2018
EP 3372302 9/2018
FR 2940764 7/2010
RU 2004233 12/1993

(56) References Cited

FOREIGN PATENT DOCUMENTS

| | | | | |
|---|---|---|---|---|
| RU | 2047330 | | 11/1995 | |
| RU | 2100295 | | 12/1997 | |
| RU | 20256 | U1 | 10/2001 | |
| RU | 22434 | | 4/2002 | |
| RU | 2199377 | C1 | 2/2003 | |
| RU | 2287490 | C1 | 11/2006 | |
| RU | 2297389 | | 4/2007 | |
| RU | 2363663 | | 9/2007 | |
| RU | 2006105261 | | 9/2007 | |
| RU | 2331586 | | 11/2007 | |
| RU | 2323036 | | 1/2008 | |
| RU | 2006121054 | | 1/2008 | |
| RU | 2323766 | | 5/2008 | |
| RU | 74909 | | 7/2008 | |
| RU | 89097 | U1 | 11/2009 | |
| RU | 2421270 | | 6/2011 | |
| RU | 2473472 | | 1/2013 | |
| RU | 2484884 | | 6/2013 | |
| RU | 2494971 | C2 | 10/2013 | |
| RU | 2531392 | | 10/2014 | |
| RU | 2614705 | | 3/2017 | |
| RU | 2015137550 | | 3/2017 | |
| SU | 1764094 | | 9/1992 | |
| WO | 8502783 | | 7/1985 | |
| WO | 9947226 | | 9/1999 | |
| WO | 0076639 | | 12/2000 | |
| WO | 02055182 | | 7/2002 | |
| WO | 2002055182 | | 7/2002 | |
| WO | WO-02055182 | A1 * | 7/2002 | ............. B01D 65/02 |
| WO | 2010122336 | | 10/2010 | |
| WO | 2011110585 | | 9/2011 | |
| WO | WO-2012112045 | A3 * | 11/2012 | ................ C02F 9/00 |
| WO | 2015083717 | | 6/2015 | |
| WO | 2015121821 | | 8/2015 | |
| WO | 2016108733 | | 7/2016 | |
| WO | 2017039485 | | 3/2017 | |

OTHER PUBLICATIONS

International Search Report for PCT/RU2016/000464 mailed Jan. 19, 2017; 1 page.

International Search Report for PCT/RU2015/000890 mailed Apr. 21, 2016, 1 page.

International Search Report for PCT/RU2015/000522 mailed Dec. 24, 2015, 2 pages.

Supplemental European Search Report and Written Opinion for EP15875786 dated May 16, 2018; 7 pages.

International Search Report for PCT/RU2019/000309 dated Aug. 13, 2019; 2 pages.

International Search Report in corresponding International Application No. PCT/RU2015/000216, mailed Aug. 13, 2015, 3 pages.

International Report on Patentability in corresponding International Application No. PCT/RU2015/000216, mailed Jul. 8, 2015, 6 pages.

Supplemental European Search Report for EP15807541 mailed Feb. 15, 2018; 2 pages.

Written Opinion of the International Searching Authority for EP15807541 mailed Feb. 15, 2018; 5 pages.

Written Opinion of the International Searching Authority for PCT/RU2015/000216 mailed Aug. 13, 2015; 6 pages.

International Report on Patentability in corresponding International Application No. PCT/RU2015/000890 mailed Jul. 18, 2017; 6 pages.

International Extended Search Report in International Application No. PCT/RU2015/000890 mailed May 25, 2018; 6 pages.

International Prelminary Report on Patentability and Written Opinion of the International Search Authority for PCT/RU2016/000466 issued Mar. 6, 2018; 5 pages.

WO2015121821; EPO Machine Translation (Year: 2020).

FR2940764A 1—EPO Machine Translation (Year: 2020).

* cited by examiner

METHOD FOR PURIFYING LIQUID AND SYSTEM FOR THE IMPLEMENTATION THEREOF

CROSS REFERENCE TO RELATED APPLICATIONS

This patent application is the national phase of PCT/RU2015/000216 filed Apr. 6, 2015, which claims the benefit of Russian Patent Application No. 20140123820 filed Jun. 10, 2014.

TECHNICAL FIELD

The group of inventions relates to technologies for the purification and/or desalination of liquids, preferably water for domestic and/or drinking water supply with recirculation and air starting. The group of inventions is intended for use in domestic and/or industrial conditions, in allotments and gardens.

BACKGROUND

Methods for the reverse osmosis purification of liquids with recirculation and systems for implementing the same are sufficiently wide spread.

Known from the prior art are solutions according to U.S. Pat. No. 4,262,346 (IPC B01D 13/00, published on Dec. 2, 1986), U.S. Pat. No. 7,338,595 B2 (IPC B01D 35/027, published on Mar. 4, 2008), RU 2287490 (IPC C02F 1/44, published on Nov. 20, 2006), U.S. Pat. No. 7,628,921 B2 (IPC C02F 1/44, published on Dec. 8, 2009) and according to publication US 2013/0334115 A1 (IPC B01D 61/02, published on Dec. 19, 2013). The disadvantage of said inventions is that a liquid is filtered by hydraulic energy generated by a pump or by a system of pumps.

Known from the prior art is a liquid purification system according to DE Patent 10 2006 015 675 A1 (IPC B01D 61/08, B01D 61/10, published on Oct. 11, 2007), wherein a pressure required to filter a liquid is generated by a liquid pressure energy. The main disadvantage of the system is the complicated structure of a liquid purification unit included in the system.

The disadvantages of the above-listed solutions were partially eliminated in the prior art liquid purification system with recirculation and air starting according to Application US2011/0198275 (IPC C02F 1/44, published on Sep. 18, 2011), selected by us as the closest prior art. The liquid purification system according to Application US2011/0198275 includes: a liquid purification unit comprising one recirculation unit consisting of a raw liquid container, a recirculation line including, contrary to the invention, a non-pressure recirculation container and a manually operated valve, and a system of valves; and a filtration unit consisting of at least one reverse osmosis device, a line for supplying a liquid from the raw water container to a fine liquid purification device, wherein the liquid purification unit is connected to a raw liquid unit, a pure liquid unit and a pressure generation means capable of generating a pressure in the recirculation unit by use of a compressed gas energy. The raw liquid unit includes a means for supplying the liquid from various sources. The raw liquid unit is coupled to the liquid purification unit via the non-pressure recirculation container included in the recirculation line. The pure liquid unit includes a pure liquid accumulation container. The pure liquid unit further includes at least one postfilter comprising sorption materials, including activated carbon.

A method for purifying a liquid intended to be implemented by the liquid purification system according to Application US2011/0198275 consists in a pneumatically-started cycle for filtering a liquid with recirculation.

1. The first stage of the cycle comprises filling with a raw liquid a raw liquid container being included in a recirculation unit included in a liquid purification unit. In doing so, the step of filling the raw liquid container is performed as follows: first, there is the step of filling a non-pressure recirculation container with the raw liquid from a raw liquid unit; after filling the non-pressure recirculation container, there are the step of stopping the supply of the raw liquid from the raw liquid unit and then the step of switching over a manually operated valve included in a recirculation line, and the raw liquid flows out of the non-pressure recirculation container into the raw liquid container, followed by the step of switching over a manually operated valve included in a recirculation line so as to cut off the ability of supplying the liquid into the raw liquid container via recirculation. The switching of the manually operated valve over to stop the supply of the liquid from the recirculation line is the obligatory process of a first stage of the filtration cycle because the leak-tightness of the container for the raw liquid is important to implement the second stage of the filtration cycle. After filling the raw liquid container with the raw liquid, there is the step of imparting the compressed gas energy by a pressure generation means to the recirculation unit, and said energy establishes a recirculation unit pressure sufficient for filtering the liquid at the second stage of the cycle in a liquid filtration unit, wherein the raw liquid container is embodied such that—aftertransmission of the compressed gas energy from the pressure generation means at the first stage of the cycle—the raw liquid container becomes leak-proof due to the compressed gas energy.
2. The second stage of the liquid filtration cycle comprises the step of supplying the raw liquid from the raw liquid container through a liquid supply line to a reverse osmosis device where the filtering is performed with extraction of a pure liquid into a pure liquid unit. In doing so, gradually reduction in a pressure in the liquid purification unit takes place. With this, a drain liquid arrives from the reverse osmosis device at the recirculation line and is accumulated in the non-pressure recirculation container where it is mixed with a new portion of raw water from the raw water unit. The accumulation of the drain liquid in the non-pressure recirculation container results in liquid flow velocity losses. The liquid filtration is periodical during the second stage of the cycle. In doing so, at the moment of stopping the filtration, there are the steps of: switching over the manually operated valve included in the recirculation line, filling the raw liquid container with the drain liquid accumulated in the non-pressure recirculation container, switching over the manually operated valve to stop the supply of the liquid from the recirculation line and to provide the repeated supply of the compressed gas energy from the pressure generation means to the recirculation unit. The second stage of the filtration cycle continues till a pure liquid accumulation container is filled with a pure liquid.

The main disadvantage of the closest prior art according to Application US2011/0198275 is that the liquid purification unit is implemented without the capability of maintaining the liquid flow velocity during the second stage of the liquid filtration because of which the filtration process at the second stage of the liquid filtration goes periodically and requires higher energy consumption than the continuous process. Simultaneously, the disadvantage of the invention according to Application US2011/0198275 is the need to add the raw liquid to the drain liquid during the second stage of the liquid filtration, which decreases the raw liquid utilization rate. Along with this, the accumulation of the drain liquid in the non-pressure recirculation container and the ability to return the drain liquid into the raw liquid container only periodically and in large portions leads to jumps of an impurity concentration in a liquid to be filtered which in turn leads to reduction in the liquid purification efficiency.

SUMMARY

It is a common object for the group of inventions and a technical result accomplished using the group of inventions to provide the novel energy-efficient liquid purification method and system which allow improvement in the energy efficiency of the liquid purification with simultaneous improvement in the degree of purification and the degree of utilization of the raw liquid.

Said object and the required technical result are accomplished by that a method for purifying a liquid involves a three-stage pneumatically-started liquid filtration cycle, said cycle making it possible to return all drain liquid into a purification system continuously prior to completion of the liquid filtration cycle and being carried out with recirculation, wherein the first stage of the cycle comprises filling with a raw liquid a raw liquid container being a part of a liquid recirculation unit included in a liquid purification unit, followed by imparting a compressed gas energy to the recirculation unit by means of a pressure generation means, said energy establishing a liquid recirculation unit pressure sufficient for liquid filtration to run in a filtering unit being a part the purification unit at the second stage of the cycle, wherein the step of transmitting a compressed gas or compressed gas and liquid mixture energy at the first stage of the filtration cycle is carried out, but is not limited only to, via a gas and liquid-impermeable partition being a part of the raw liquid container being a part of the recirculation unit included in the liquid purification unit. In doing so, at least a larger part of the raw liquid arrives at the recirculation unit preferably at the first stage of the liquid filtration cycle. At the same time, at the second stage of the cycle the liquid filtration goes with continuous recirculation while maintaining a high liquid flow velocity so as to control a rate of supplying the liquid into a liquid filtration unit from the liquid recirculation unit while the drain liquid is directly supplied under pressure through the recirculation line to the raw liquid container from the liquid filtration unit with simultaneous stirring of the raw and drain liquids. Further, the third stage of the cycle in the claimed liquid purification method comprises removing a residual drain water from the raw liquid container due to the compressed gas or compressed gas and liquid mixture energy, wherein completion of the third stage can be followed by repetition of the liquid filtration cycle without intermediate preparation steps beginning from the first stage; the third stage of the liquid filtration cycle also comprises further recovering a system energy in the form of the compressed gas or compressed gas and liquid mixture energy; in addition, the third stage of the cycle further comprises reverse washing a fine liquid purification device. The liquid filtration cycle can further include a pure liquid conditioning and/or mineralization process. With this, the claimed liquid purification system includes a liquid purification unit comprising, for example, one or two recirculation units consisting of a raw liquid container, a recirculation line, a system of valves, and a filtration unit, consisting, for example, of one fine liquid purification device which can be embodied as a reverse-osmosis or nanofiltration device, a line for supplying the liquid from the raw water container to the fine liquid purification device, wherein the liquid purification unit is connected to a raw liquid unit, a pure liquid unit and a pressure generation means capable of, but not limited only to, generating a recirculation unit pressure using a compressed gas energy, said system including a liquid purification unit capable of carrying out a three-stage liquid filtration cycle, said cycle making it possible to return all drain liquid into the purification system prior to completion of the liquid filtration cycle and being carried out with continuous recirculation while maintaining a high liquid flow velocity so as to control a rate of supplying the liquid into the liquid filtration unit from the liquid recirculation unit while the drain liquid is directly supplied under pressure through a recirculation line to the raw liquid container from the fine liquid filtration device with simultaneous stirring of the raw and drain liquids, wherein the pressure generation means is capable of generating the recirculation unit pressure using the compressed gas and liquid mixture energy. At the same time, the liquid purification unit is capable of being directly coupled to the raw liquid container of the recirculation line directed from the fine liquid purification device, wherein the raw liquid container included in the recirculation unit included in the liquid purification unit is capable of removing the drain water from the raw liquid container due to the compressed gas or compressed gas and liquid mixture energy at the third stage of the cycle and further is capable of converting a system energy into the compressed gas or compressed gas and liquid mixture energy at the third stage of the cycle; the raw liquid container is also provided with a gas and liquid-impermeable partition which can be embodied, for example, as an elastic diaphragm through which the compressed gas or compressed gas and liquid mixture energy is transmitted to the system and conversion of system energy into the compressed gas or compressed gas and liquid mixture energy can be further carried out at the third stage of the filtration cycle; also, the liquid-impermeable partition, for example, passes the compressed gas and/or is provided with a compressed gas supply opening and/or valve; in this case, the compressed gas arriving at the raw liquid container from the pressure generation means is an antiscalant or a coagulant; furthermore, the raw liquid container is capable of providing the flow-through movement of the liquid; at the same time the raw liquid container further comprises a restrictor which does not permit the raw liquid to fill the raw liquid container in the amount more than a defined one. The system of valves included in the recirculation unit included in the purification unit is capable of directing the compressed gas or compressed gas and liquid mixture flow at the first stage of the liquid filtration cycle from the output of the pressure generation means to the raw liquid container included in the recirculation unit, and is further capable of directing the compressed gas or compressed gas and liquid mixture flow at the third stage of the filtration cycle from the raw liquid container included in the recirculation unit to an input of the pressure generation means or is further capable of directing the compressed gas or compressed gas and liquid mixture flow from the raw liquid container being a part of one recirculation unit to the raw liquid container being a part of another recirculation unit. The liquid supply line included in the liquid filtration unit included in the liquid purification unit also is provided with a liquid circulation means; the recirculation line further comprises, for example, one filtration device while the raw liquid unit also comprises further, for example, one prefilter and/or an antiscalant dosing unit which provides dosage of a certain amount of the antiscalant at the first stage of the liquid filtration cycle and maintenance preferably of all amount of the antiscalant arrived from the raw water unit at the first stage of the cycle, within a water purification unit, thereby to provide increase in the concentration of the antiscalant in a liquid present in the recirculation unit along with growth of the impurity concentration in the liquid present in the recirculation unit throughout the second stage of the liquid filtration cycle; in addition, the raw liquid unit further comprises a unit for dosing auxiliary substances for purification while the pure liquid unit further comprises, for example, one postfilter comprising sorption materials and/or a mineralization unit and/or an additional liquid preparation unit; also, the pure liquid unit further comprises an inverse washing unit of the fine liquid purification device included in the recirculation unit.

DETAILED DESCRIPTION

Figure 1:
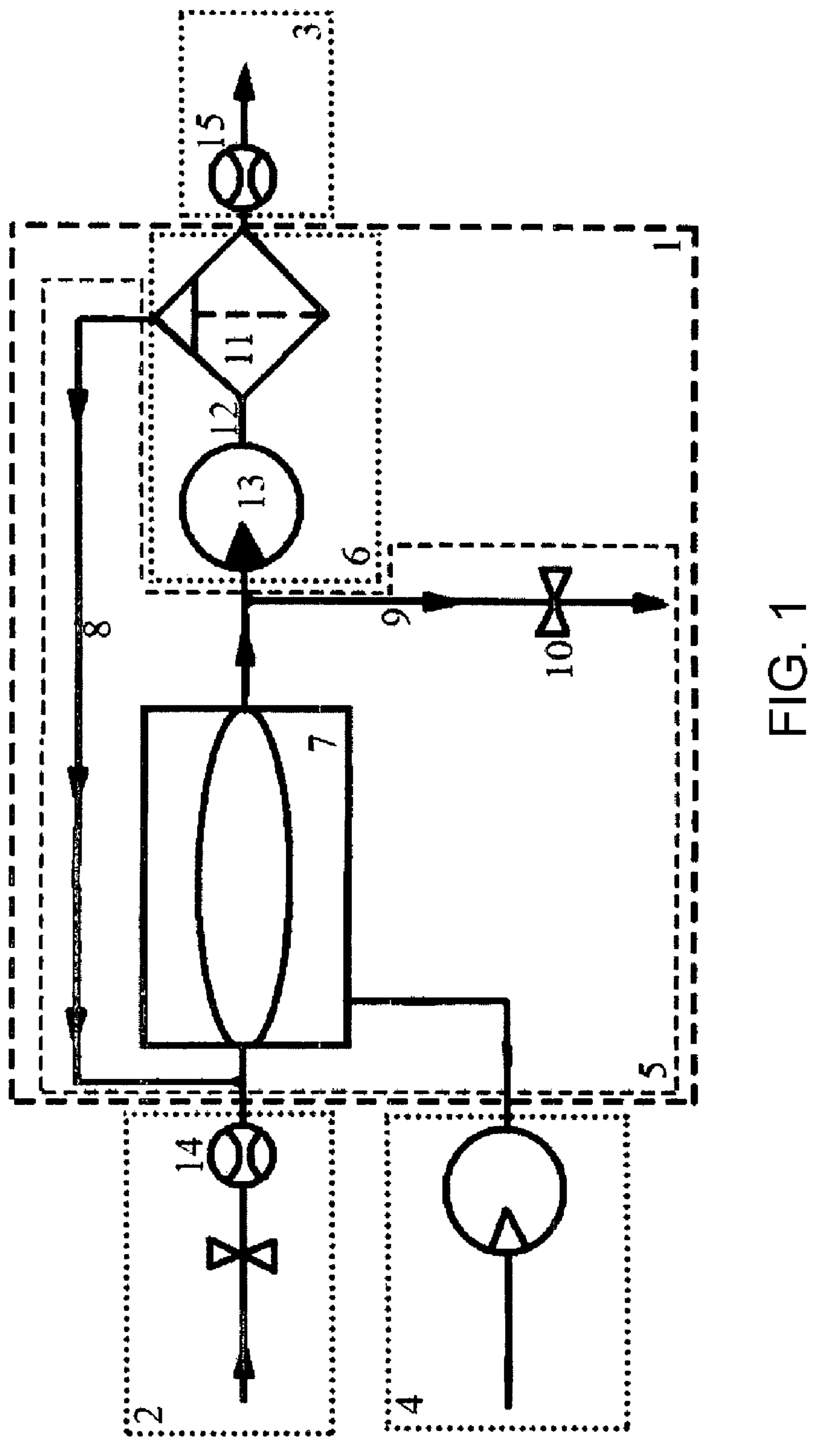
FIG. 1 shows a schematic lay-out diagram illustrating basic members of a liquid purification system embodied with one recirculation unit included in a water purification unit.

Generally, a liquid purification system (FIG. 1) includes a liquid purification unit (1), a raw liquid unit (2), a pure liquid unit (3), a pressure generation means (4). At the same time, the liquid purification unit (1) is connected to the raw liquid unit (2), the pure liquid unit (3), and the pressure generation means (4).

The liquid purification unit (1) includes at least one liquid recirculation unit (5) and a liquid filtration unit (6).

The liquid filtration unit (6) includes, for example, one fine liquid purification device (11) embodied, for example, as a reverse-osmosis or nanofiltration device. The fine liquid purification device (11) has one input coupled to a line (12) for supplying a liquid from the raw water container (7) included in the recirculation unit (5), wherein—contrary to the closest prior art—the liquid supply line (12) comprises a liquid circulation means (13), for example, a diaphragm or centrifugal low-power pump or injector. The fine liquid purification device has two outputs: a pure liquid output coupled to the pure liquid unit (3) and a drain liquid output coupled to a recirculation line (8) included in the recirculation unit (5).

Each liquid recirculation unit (5) included in the liquid purification unit includes the raw liquid container (7), the recirculation line (8), a system of valves (10) and—contrary to the closest prior art—a drain line (9). The raw liquid container (7) is made of polymeric materials or a metal and—contrary to the closest prior art—is capable of providing the flow-through movement of the liquid, in other words, the raw liquid container (7) has an input coupled simultaneously to the raw liquid unit (2) and directly to the recirculation line (8) and an output coupled to the liquid supply line (12) included in the liquid filtration unit (6). The raw liquid container (7) is also coupled to the pressure generation means (4), wherein the compressed gas or compressed gas and liquid mixture energy is transmitted from the pressure generation means to the raw liquid container (7) through a gas and liquid-impermeable partition being a part of the raw liquid container (7). Said partition can be embodied, for example, as an elastic diaphragm or as a solid partition operated on the principle of a piston. Said partition also can be impermeable for a liquid but permeable for a compressed gas and/or can comprise a compressed gas supply opening and/or valve, wherein the compressed gas arriving at the raw liquid container can be an antiscalant or a coagulant. For example, carbon dioxide can be used as the compressed gas; in such a case, when carbon dioxide penetrates through the gas-permeable partition and/or the opening and/or valve, it is mixed with the raw water which leads to reduction in pH (a hydrogen index) of the raw water; this reduces the precipitation of sediments on system members. Or, for example, oxygen can be used as the compressed gas; in such a case, when oxygen penetrates through the gas-permeable partition and/or opening and/or valve, it is mixed with the raw water accelerating the iron oxidation process. The raw liquid container (7) can further comprise an adjustable restrictor, for example, a movable rigid partition or valve (not shown in the figures); in this case, a maximum raw liquid volume which can be placed in the raw liquid container is set by the restrictor. Contrary to the closest prior art, the raw liquid container (7) is implemented so as to fulfill two functions simultaneously: the function of transmitting the compressed gas or compressed gas and liquid mixture energy from the pressure generation means (4) to the liquid being in the present container, and the function of mixing the raw liquid and the drain liquid. The raw liquid container in the closest prior art is capable of implementing only the function of transmitting the compressed gas energy from the pressure generation means to the liquid being in the raw liquid container. Contrary to the closest prior art, the recirculation unit (5) comprises also the drain line (9). The recirculation line can further include a filtration device (not shown in the figures), for example, an ultrafiltration or microfiltration device, a sorption filter. The recirculation unit is controlled by the system of valves (10) which can consist, for example, of manually operated valves or automatic control valves controlled by a programmed device. In such a case, the system of valves (10) is capable of directing a compressed gas or compressed gas and liquid mixture flow at the first stage of the liquid filtration cycle from the output of the pressure generation means (4) to the raw liquid container (7) included in the recirculation unit (5), and further is capable of directing the compressed gas or compressed gas and liquid mixture flow at the third stage of the filtration cycle from the raw liquid container (7) included in the recirculation unit to the input of the pressure generation means (4), or—if the water purification system is embodied with at least two recirculation units (5) included in the liquid purification unit (1) (FIG. 2)—the system of valves (10) is embodied with a further capability of directing the compressed gas or compressed gas and liquid mixture flow from the raw liquid container (7) being a part of one recirculation unit (5) to the raw liquid container (**7*a*) being a part of another recirculation unit (5*a***).

The raw liquid unit (2) includes at least, one means for supplying the liquid from various sources, for example, a city water system or well, and at least one raw liquid amount measurement means (14). Further, the raw liquid unit (4) can comprise an antiscalant dosing unit (not shown in the figures) and/or a unit for dosing auxiliary substances for purification (not shown in the figures), for example, coagulants, oxidants or catalysts.

The pure liquid unit (3) can be embodied as a pure liquid reservoir or a line for supplying the pure liquid to a user. The pure liquid unit comprises at least one pure liquid amount measurement means (15). Further, the pure liquid unit (3) can include at least one postfilter comprising sorption materials (not shown in the figures) and/or a mineralization unit (not shown in the figures) and/or an additional liquid preparation unit (not shown in the figures), for example, a sterilizer or a device for saturation of the liquid with oxygen. Furthermore, the pure liquid unit can comprise a reverse washing unit (not shown in the figures) of the fine liquid purification device, for example, a hydro-pneumatic accumulator or a line for supplying pure liquid to the fine liquid purification device.

The raw and pure liquid amount measurement means (14) and (15) are intended for the monitoring of the raw and pure liquid amount. Based on the difference of these indices, it is possible to determine a degree of utilization of the raw liquid, in other words, an amount of the pure liquid produced of a fixed amount of the raw liquid. The degree of utilization of the raw liquid is set depending upon the needs of the pure liquid and the degree of availability of raw liquid sources and can be a controlling parameter for the liquid filtration cycle. In case when the raw liquid container included in the recirculation unit included in the liquid purification system is embodied with an adjustable restrictor while the pure liquid line includes a pure liquid reservoir having a fixed volume, the degree of utilization of the raw liquid can be set through a maximum amount of the raw liquid which can be placed in the raw liquid container and within the volume of a pure liquid reservoir.

The pressure generation means (4) can be, but not limited only to, a system for supplying compressed gas including, but not limited only to, air, nitrogen, steam, oxygen, carbon dioxide; a compressed gas, for example, air, nitrogen, carbon dioxide or oxygen, cylinder; or a compressor; or a compressed gas and liquid mixture supply device; or a steam generator.

Within the distinguishing features, the liquid purification method intended to be implemented by the above described liquid purification system consists in a three-stage pneumatically-started liquid filtration cycle with recirculation, wherein:

1. At the first stage of the liquid filtration cycle, a certain amount (V) of the raw liquid with an amount ($C_0$) of impurities arrive—via an input coupled to the raw liquid unit (2)—at the raw liquid container (7) included in the liquid recirculation unit (5) included in the purification unit (1), wherein the raw liquid amount measurement means (14) fixes the amount of the raw liquid. In doing so, a pressure in the liquid purification unit (1) is lower than that in the raw liquid unit (2), therefore, filling of the raw liquid container (7) occurs without additional consumption of energy. After completion of filling the raw liquid container (7) with the raw liquid in the amount (V) with the pressure generation means (4), the compressed gas or compressed gas and liquid energy is imparted to the recirculation unit (5), which establishes a pressure in the water recirculation unit (1), said pressure being sufficient for filtration to run at the second stage of the cycle. Further, addition of the antiscalant to the raw liquid using an antiscalant dosing unit is possible at the first stage of filtration, the latter unit being a part of the raw liquid unit (2). Further, addition of auxiliary substances for purification using an auxiliary-substances-for-purification dosing unit (not shown in the figures) is possible at the first stage of filtration, the latter unit being a part of the raw liquid unit.
2. At the second stage of the liquid filtration cycle, the raw liquid at a pressure P arrives from the raw liquid container (7) at the liquid supply line (12) being a part of the liquid filtration unit where acquires a flow velocity (v) by means of the liquid circulation means (13). The structure of the closest prior art has no liquid circulation means, therefore, the pressure generation means fulfills the flow velocity creation function, which does not allow a high liquid flow velocity and also requires consumption of a compressed gas energy higher than that required in implementation of the claimed group of inventions. The liquid arrives through the supply line (12) at an input of the fine liquid purification device (11) where as a result of the filtration process formed is a pure liquid arriving through a pure liquid output at the pure liquid unit (3). The pure liquid amount measurement means (15) included in the pure liquid unit (3) fixes an amount of the pure liquid. The drain liquid having a volume $V_1$ ($V_1<V$) with an impurity concentration $C_1$ ($C_1>C_0$) arrives at the recirculation line (8) and returns directly into the raw liquid container (7) from which it again arrives at the liquid supply line (12). In doing so the energy loss in the system is not more than necessary to extract the pure liquid to the pure liquid unit. The system pressure remains sufficient for filtration while the flow velocity is still high. Thus, the energy efficiency of the liquid purification becomes higher. At the same time, the raw and drain liquids are continuously stirred in the raw liquid container (7), which provides uniform increase in the concentration of impurities in the liquid supplied to the fine liquid purification device (11). Uniform, rather than jump-wise as in the closest prior art, increase in the concentration of impurities in the liquid supplied to the fine liquid purification device (11) improves the liquid purification efficiency. The increase in a liquid supply rate is possible at the second stage of the cycle at any time due to feed of an additional energy to the system from the pressure generation system (4).

The second stage of the cycle continues uninterruptedly and not periodically as in the closest prior art until the amount of the drain liquid achieves a predetermined amount $V_N$ determined from a difference between an amount of the raw liquid fixed by the raw liquid amount measurement means (14) and an amount of the pure liquid fixed by the pure liquid amount measurement means (15). The continuous progress of the second filtration stage in the invention selected as the closest prior art is impossible, and also the structure of the closest prior art assumes periodical addition of the raw liquid to the liquid purification unit from the raw liquid unit during the second stage of the filtration cycle.

Figure 2:
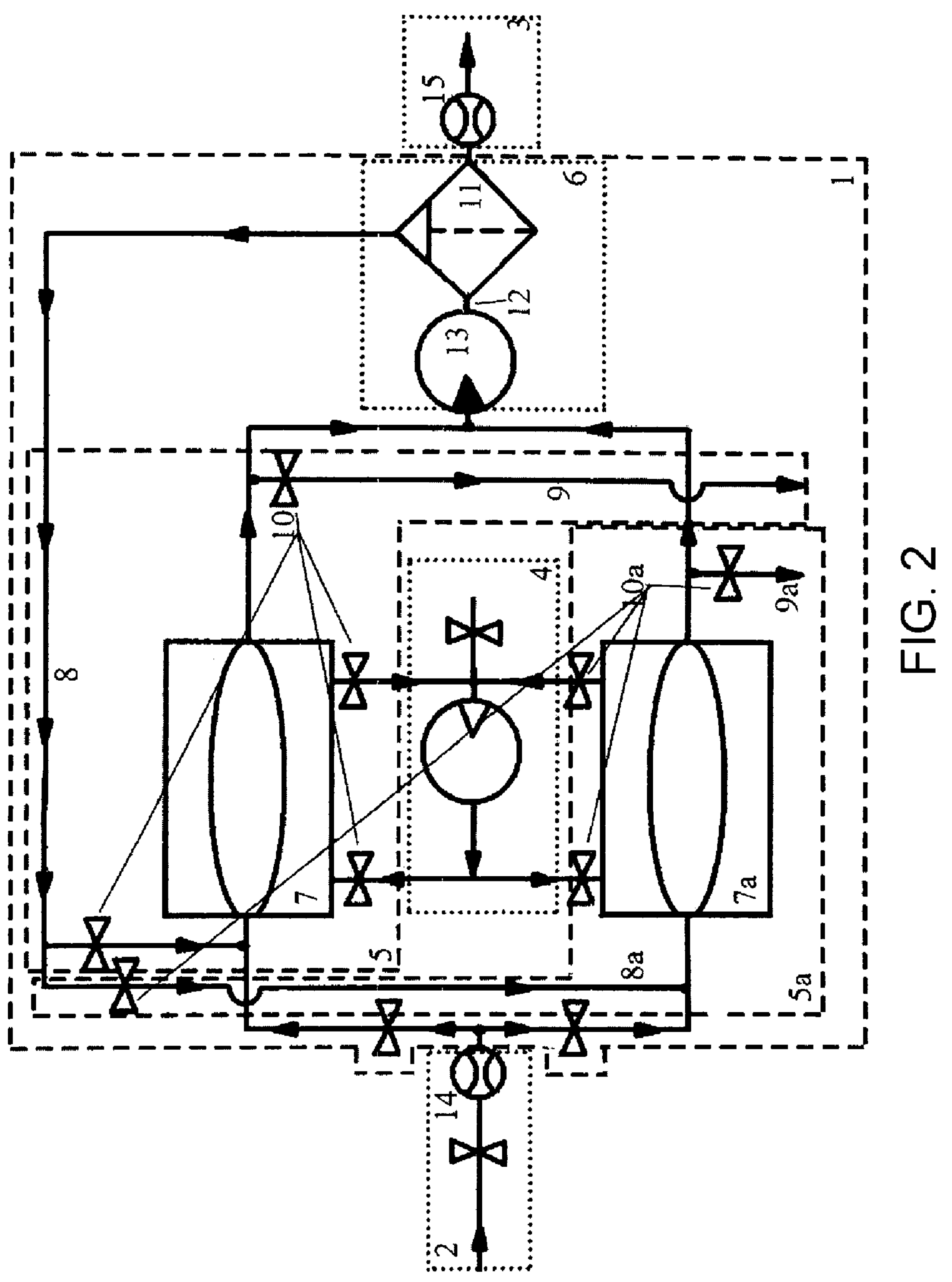
FIG. 2 shows a schematic lay-out diagram illustrating basic members of a liquid purification system embodied with two recirculation units included in a water purification unit.

3. The partial pressure relief takes place in the liquid purification unit (1) at the third stage of the cycle. The energy resulted from the pressure relief in the purification unit (1) can be recovered in the form of the compressed gas or compressed gas and liquid mixture energy. At the same time, the system of valves (10) is capable of directing the compressed gas or compressed gas and liquid mixture flow from the raw liquid container (7) included in B recirculation unit (5) to the input of the pressure generation means (4) or to another recirculation unit if the purification system is embodied with at least two recirculation units in the purification unit (FIG. 2). Due to the compressed gas or compressed gas and liquid mixture energy remained in the purification unit (1), the drain liquid residual in the raw liquid container (7) in the amount $V_N$ at the impurity concentration $C_N$ ($C_N > C_0$) is completely released into the drain piping through the drain line (9). In doing so, it is possible to set any amount $V_N$ depending upon an initial impurity concentration $C_0$ and a pure liquid need. If necessary, the amount $V_N$ can be small as compared to the initial amount V, therefore, the residual compressed gas or compressed gas and liquid mixture energy necessary to release the liquid in the amount $V_N$ to the drain piping can be minimum, and practically the complete recovery of the system energy takes place. It is possible to vary the sequence of processes at the third stage of the filtration cycle, if necessary; in this case, first, the release of the drain liquid remained in the raw liquid container (7) takes place through the drain line (9) at the third stage of the filtration cycle due to the compressed gas or compressed gas and liquid mixture energy. Then, the residual energy recovery takes place. Thus, the energy efficiency of the liquid filtration increases. At the same time, after release of the liquid in the amount $V_N$ to the drain piping the raw liquid container (7) becomes empty, while the pressure in the purification unit (1) becomes lower than that in the raw liquid unit (2). The repetition of the liquid filtration cycle is possible beginning from the first stage without intermediate preparation steps. Further, the reverse washing of the fine liquid filtration device (11) is possible at the third stage of liquid filtration by means of an inverse washing unit (not shown in the figures) included in the pure liquid unit (3).

Within the distinguishing features of the claimed invention, the liquid purification system can further comprise an antiscalant dosing unit (not shown in the figures) arranged in the raw liquid unit (2) and embodied so as to dose a certain amount of the antiscalant into a defined amount of the raw liquid at the first stage of the filtration cycle. In doing so, the antiscalant does not enter the pure liquid during the filtration cycle. Thus, the concentration of the antiscalant in the drain liquid increases simultaneously with increase of the impurity concentration. Therefore, the more effective action of the antiscalant is provided owing to which the service life of the fine liquid purification device (11) increases.

Further, within the distinguishing features of the claimed invention, the liquid purification system with at least two recirculation units within the liquid purification unit (FIG. 2) is capable of starting the first stage of the liquid filtration cycle in each subsequent recirculation unit in parallel with the third stage of liquid filtration in a previous recirculation unit, which makes it possible to supply the pure liquid to a consumer continuously without the need to include a pure liquid reservoir in the pure liquid unit.

This description of the present invention discloses a preferred embodiment of the invention. It can be changed within the disclosed set of claims, so the wide use of the invention is possible.

The invention claimed is:

1. A method for purifying a liquid in a pneumatically-started liquid filtration cycle with recirculation having a first stage, a second stage, and a third stage, the method comprising:

in the first stage, filling a raw liquid container being a part of a liquid recirculation unit included in a liquid purification unit, wherein the raw liquid container is filled with a raw liquid comprising raw water, in the second stage after the first stage, using a pressure generation means disposed outside of the raw liquid container to impart a compressed gas energy to the liquid recirculation unit including to the raw liquid container, and said compressed gas energy establishes a liquid recirculation unit pressure sufficient for moving the raw liquid to a filtration unit of the liquid purification unit, the filtration unit using a liquid circulation means to move the raw liquid at a velocity to at least one fine liquid purification device configured to purify the raw liquid and thereby produce drain liquid, in the third stage, returning the drain liquid into the raw liquid container using the liquid circulation means via a recirculation line from the at least one fine liquid purification device continuously during filtering of the raw liquid for mixture with the raw liquid in the raw liquid container;

removing residual drain liquid from the raw liquid container via a drain line due to the compressed gas energy, wherein completion of the third stage is followed immediately by repetition of the liquid filtration cycle of the first stage;

wherein the imparting the compressed gas energy further comprises transmitting energy from a compressed gas or compressed gas in a liquid mixture through at least a gas and liquid-impermeable partition of the raw liquid container via pressure applied to the gas and liquid-impermeable partition by the compressed gas or compressed gas in a liquid mixture.

2. The method for purifying the liquid according to claim 1, further comprising receiving at least more than half of the raw liquid to be processed at the recirculation unit at the first stage of the liquid filtration cycle prior to an initial imparting of the compressed gas energy.

3. The method for purifying the liquid according to claim 1, further comprising carrying out the second stage of the liquid filtration cycle with continuous recirculation while maintaining a liquid flow velocity so as to control a rate of supplying the liquid into the liquid filtration unit from the liquid recirculation unit while the drain liquid is directly supplied under pressure through the recirculation line to the raw liquid container from the liquid filtration unit while simultaneous stirring of the raw liquid and the drain liquid.

4. The method for purifying the liquid according to claim 1, further comprising recovering a system energy from the compressed gas or compressed gas and liquid mixture energy at the third stage of the liquid filtration cycle.

5. The method for purifying the liquid according to claim 1, further comprising reverse washing a fine liquid purification device at the third stage of the liquid filtration cycle.

6. The method for purifying the liquid according to claim 1, further comprising performing a mineralization process.

7. A liquid purification system comprising:

a liquid purification unit comprising:

at least one recirculation unit comprising a raw liquid container, a recirculation line, and a system of valves, and a filtration unit comprising at least one fine liquid purification device configured to purify raw water and a liquid circulation means, a line for supplying fluid comprising the raw water from the raw liquid container to the at least one fine liquid purification device, a pure liquid unit, a pressure generation means disposed outside of the raw liquid container and for generating a pressure using a compressed gas energy to pressurize the raw liquid container to move the fluid from the raw liquid container to the filtration unit during a second stage of a three-stage liquid filtration cycle, and the liquid circulation means for moving the fluid to the at least one fine liquid purification device and for generating a recirculation unit pressure that pressurizes the recirculation line to move drain liquid from the at least one fine liquid purification device to the raw liquid container during the second stage of the three-stage liquid filtration cycle, wherein the liquid purification unit is configured to perform the three-stage liquid filtration cycle and to return the drain liquid into the raw liquid container prior to completion of the liquid filtration cycle with continuous recirculation while maintaining a liquid flow velocity so as to control a rate of supplying the fluid into the liquid filtration unit from the liquid recirculation unit while the drain liquid is directly supplied under pressure through the recirculation line to the raw liquid container from the at least one fine liquid purification device while simultaneous stirring of the raw water and the drain liquid within the raw liquid container, wherein the raw liquid container is configured to remove the drain liquid from the raw liquid container using the compressed gas or compressed gas and liquid mixture energy at a third stage of the cycle, and is further configured to convert a system energy into the compressed gas or compressed gas or liquid mixture energy at the third stage of the cycle, wherein the raw liquid container comprises a gas- and liquid-impermeable partition disposed such that the compressed gas or compressed gas and liquid mixture energy is transmitted to the system through the gas- and liquid-impermeable partition, and through which further conversion of a system energy into the compressed gas or compressed gas and liquid mixture energy occurs during the third stage of the filtration cycle.

8. The liquid purification system according to claim 7, wherein the liquid purification unit includes at least two recirculation units.

9. The liquid purification system according to claim 7, wherein the pressure generation means is configured to generate a pressure in the recirculation unit using a compressed gas and liquid mixture energy.

10. The liquid purification system according to claim 7, wherein the gas- and liquid-impermeable partition comprises an elastic diaphragm.

11. The liquid purification system according to claim 7, wherein the raw liquid container is configured to provide a flow-through movement of the liquid.

12. The liquid purification system according to claim 7, wherein the raw liquid container further comprises an adjustable restrictor.

13. The liquid purification system according to claim 7, wherein the system of valves is configured to direct a compressed gas or compressed gas and liquid mixture flow at a first stage of the liquid filtration cycle from an output of the pressure generation means to the raw liquid container included in the recirculation unit.

14. The liquid purification system according to claim 8, wherein the system of valves is configured to direct a compressed gas or compressed gas and liquid mixture flow from the raw liquid container being a part of one recirculation unit to the raw liquid container being a part of another recirculation unit.

15. The liquid purification system according to claim 7, wherein the fine liquid purification device comprises a nanofiltration device.

16. The liquid purification system according to claim 7, wherein the recirculation line included in the liquid recirculation unit further comprises at least one filtration device.

17. The liquid purification system according to claim 7, wherein the raw liquid unit further comprises at least one prefilter.

18. The liquid purification system according to claim 7, wherein the pure liquid unit further comprises at least one postfilter comprising at least one of sorption materials or an additional liquid preparation unit.

* * * * *